(12) United States Patent
Portmann et al.

(10) Patent No.: US 7,750,028 B2
(45) Date of Patent: Jul. 6, 2010

(54) CRYSTAL MODIFICATIONS OF 1-(2,6-DIFLUOROBENZYL)-1H-1,2,3-TRIAZOLE-4-CARBOXAMIDE

(75) Inventors: Robert Portmann, Pratteln (CH); Urs C Hofmeier, St. Pantaleon (CH); Andreas Burkhard, Basel (CH); Walter Scherrer, Rheinfelden (CH); Martin Szelagiewicz, Munchenstein (CH)

(73) Assignee: Novartis AG, Basel (CH)

( * ) Notice: Subject to any disclaimer, the term of this patent is extended or adjusted under 35 U.S.C. 154(b) by 133 days.

(21) Appl. No.: 11/329,945

(22) Filed: Jan. 11, 2006

(65) Prior Publication Data

US 2006/0116520 A1 Jun. 1, 2006

Related U.S. Application Data

(63) Continuation of application No. 10/787,528, filed on Feb. 26, 2004, now abandoned, which is a continuation of application No. 10/294,408, filed on Nov. 14, 2002, now abandoned, which is a continuation of application No. 09/125,329, filed as application No. PCT/EP98/03427 on Jun. 8, 1998, now Pat. No. 6,740,669.

(30) Foreign Application Priority Data

Jun. 10, 1997 (CH) ..................................... 1404/97

(51) Int. Cl.
*A61K 31/4192* (2006.01)
*C07D 249/16* (2006.01)

(52) U.S. Cl. .................. 514/359; 548/255; 548/259

(58) Field of Classification Search .................. 514/359; 548/255, 259
See application file for complete search history.

(56) References Cited

U.S. PATENT DOCUMENTS

| | | | |
|---|---|---|---|
| 3,992,378 A | 11/1976 | St. Clair | |
| 4,156,734 A | 5/1979 | Stone | |
| 4,536,518 A | 8/1985 | Welch et al. | |
| 4,789,680 A * | 12/1988 | Meier | 514/359 |
| 5,248,699 A | 9/1993 | Sysko | |
| 6,156,907 A | 12/2000 | Portmann | |
| 6,455,556 B2 | 9/2002 | Portmann | |

FOREIGN PATENT DOCUMENTS

| | | |
|---|---|---|
| DE | 4217952 | 12/1993 |
| EP | 0114347 | 12/1983 |
| EP | 0371564 | 11/1989 |
| EP | 431943 | 6/1991 |
| EP | 812320 | 8/1996 |
| GB | 1511195 | 5/1978 |
| JP | A-02/214504 | 8/1990 |
| JP | A-05/155822 | 6/1993 |
| WO | 91/01724 | 2/1911 |
| WO | WO92/07847 | 5/1992 |
| WO | 95/12417 | 5/1995 |
| WO | 96/08485 | 3/1996 |
| WO | 96/09295 | 3/1996 |
| WO | 98/056773 | 12/1998 |

OTHER PUBLICATIONS

Sicuteri "Identification of antiepileptic . . . " CA 54:112243 (1960).*
Rowland et al. "Clinical pharmacokinetics . . . " p. 123 (1995).*
Palhagen et al. "Rufinamide: a double blind . . . " Epilepsy Res. 43, p. 115-124 (2001).*
Tasso et al. "Pharmacophore . . . " J. Mo. Model 7, p. 231-239 (2001).*
Rouhi, A. Maureen. "The Right Stuff." Chem. & Engineering News, p. 32, (2003).
Concise Encyclopedia Chemistry, Walter de Gruyter, Berlin, New York, p. 82-83, (1993).
US Pharmacopia #23, National Formulary #18, p. 1843-1844, (1995).
Munzel, Prog Drug Res, 10: 227-230, (1966).
Munzel, Prog Drug Res, 14: 309-321, (1970).
Chemical Abstracts 105:48847, 1986.
Chemical Abstracts 106:182481, 1987.
Chemical Abstracts 108:118769, 1988.
Chemical Abstracts 90:192418, (1979).
Chemical Abstracts 77:168514, (1972).
Chemical Abstracts 80:100132, (1974).
Chemical Abstracts 80:6799, (1974).
Chemical Abstracts 94:180542, (1981).
Cheung, "Intra- and Inter-subject Variabilities of CGP 33101 After Replicate Single Oral Doses of Two 200-mg Tablets and 400-mg Suspension." Pharm. Res. 12(12): 1878-1882 (1995).

(Continued)

*Primary Examiner*—Celia Chang
(74) *Attorney, Agent, or Firm*—Montgomery, McCracken, Walker & Rhoads, LLP; Kristin M. Nevins; Robert R. Axenfeld

(57) ABSTRACT

The invention relates to the novel modifications B and C of the compound 1-(2,6-difluorobenzyl)-1H-1,2,3-triazole-4-carboxamide of the formula

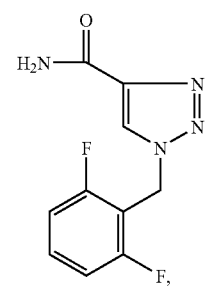

its use and pharmaceutical preparations comprising this crystal modifications.

8 Claims, 2 Drawing Sheets

OTHER PUBLICATIONS

Chemical Abstracts 104:24095, (1986).
Ulicky, Comp Dic Phys Chem, 21, (1992).
Wyngaarden et al., Cecil Textbook Medicine. P48-55 (1983).
Full Development proposal CGP33101 (2009).
Meier, Characteristics of CGP33101 Kenndaten Fuer (2009).
Energy Temperature Diagram (2009).
Dissolution profiles (2009).
Merck Index, 13th Ed. Monograph No. 8373 (2001).
Presentation on patenting polymorphs by EPO examiner (2006).
Kostic et al, Dopaminergic Ligands, Drugs Res, 44(1): 697-702, (1994).
Chemical Abstracts, 95:50317r, (1981).

* cited by examiner

CRYSTAL MODIFICATIONS OF 1-(2,6-DIFLUOROBENZYL)-1H-1,2,3-TRIAZOLE-4-CARBOXAMIDE

This application is a continuation of application Ser. No. 10/787,528, filed on Feb. 26, 2004 now abandoned, which is a continuation of application Ser. No. 10/294,408, filed on Nov. 14, 2002, now abandoned, which is a continuation of application Ser. No. 09/125,329, filed on Sep. 8, 1998, now U.S. Pat. No. 6,740,669, filed as 371 of international application No. PCT/EP98/03427, filed on Jun. 8, 1998. The entire disclosure of the prior application, U.S. application Ser. No. 10/787,528, filed Feb. 26, 2004, is considered as being part of the disclosure of the present application and is hereby incorporated by reference herein.

BACKGROUND OF THE INVENTION

The compound 1-(2,6-difluorobenzyl)-1H-1,2,3-triazole-4-carboxamide of the formula

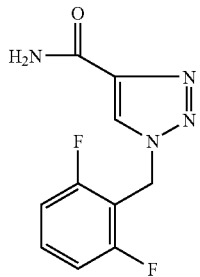

is described in the European Patent Application with the Publication No. 0 199 262 A2(EP 199262), for example in Example 4. Valuable pharmacological properties are attributed to this compound; thus, it can be used, for example, as an antiepileptic. The compound 1-(2,6-difluorobenzyl)-1H-1,2,3-triazole-4-carboxamide is obtained according to EP 199262, starting from 2,6-difluorobenzyl azide via the formation of 1-(2,6-difluorobenzyl)-1H-1,2,3-triazole-4-carboxylic acid, the procedure being analogousto Example 2.

EP 199262 provides no information at all about possible crystal modifications obtained. If the method according to Example 4 is used in conjunction with Example 2, the crude 1-(2,6-difluorobenzyl)-1H-1,2,3-triazole-4-carboxamide product obtained is finally crystallized from ethanol. However, EP 199262 gives no indication that such recrystallization is specifically to be applied, or on particular conditions that might be adopted. It has now surprisingly been found that the different crystal modifications (polymorphism) characterized below can be prepared by choice of specially selected process conditions, for example through the choice of an appropriate solvent for the recrystallization or the duration of the recrystallization.

DESCRIPTION OF THE INVENTION 1-(2,6-Difluorobenzyl)-1H-1,2,3-triazole4-carboxamide can be obtained in the novel crystal modifications A, A', B and C. These crystal modifications differ with respect to their thermodynamic stability, in their physical parameters, such as the absorption pattern of IR and Raman spectra, in X-ray structure investigations and in their preparation processes.

The invention relates to the novel crystal modifications A and A', their preparation and use in pharmaceutical preparations comprising this crystal modification.

The modification A', compared with A, has defects in the crystal lattice. These are detectable, for example, by X-ray analysis, e.g. by smaller line spacings with otherwise predominantly identical lines or bands.

The crystal modification A of 1-(2,6-difluorobenzyl)-1H-1,2,3-triazole-4-carboxamide melts at 242° C. (239-245° C.).

In the FT infrared (FT-IR) spectrum (KBr pellet—transmission method), modification A or A' differs from modifications B and C predominantly in the shape and in the relative intensity of many bands. Particularly characteristic are the bands at 3412 cm$^{-1}$ and 3092 cm$^{-1}$ [cf. FIG. 1], which are not present in the FT-IR spectra of the modifications B and C. In the range 4000-600 cm$^{-1}$, inter alia the following bands are obtained for modification A: 3412, 3189, 3092, 1634, 1560, 1473, 1397, 1325, 1300, 1284, 1235, 1125, 1053, 1036, 1014, 885, 840, 799, 781, 723, 688 and 640 cm$^{-1}$. For example, the apparatus IFS 88 (Bruker) can be used for recording of each of the FT-IR spectra.

In the FT Raman spectrum (powder—reflection method 180°), the modification A or A' differs from modifications B and C predominantly in the shape and in the relative intensity of many bands. Particularly characteristic are the band at 1080 cm$^{-1}$ [cf. FIG. 2], which is not present in the Raman spectra of the modifications B and C. In the range 3400-300 cm$^{-1}$, inter alia the following bands are obtained for the modification A: 3093, 2972, 1628, 1614, 1558, 1465, 1446, 1393, 1279, 1245, 1147, 1080, 1061, 1036, 1014, 840, 724, 691, 667, 550, 499, 437 and 368 cm$^{-1}$. For example, the apparatus RFS 100 (Bruker) can be used for recording of each of the FT Raman spectra.

The modification A has an X-ray powder pattern with characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, 2.81 Å [cf. Table 1]. The measurement can be carried out, for example, in transmission geometry on an FR 552 Guinier camera from Enraf-Nonius, Delft (The Netherlands), using copper K$\alpha_1$ radiation (wavelength $\lambda$=1.54060 Å). The patterns recorded on X-ray film were measured using an LS-18 line scanner from Johannsson, Täby (Sweden) and evaluated using the Scanpi software (P. E. Werner, University of Stockholm).

Characteristic for the modification A is the thermogram in differential scanning calorimetry. It has an endothermic peak in the range from 230° C. to 260° C. The peak temperature is 239-245° C., and the endothermic signal is 209 J/g +±10 J/g. The measurement was carried out on a Perkin Elmer DSC 7 in a closed pan with a heating rate of 20 K/minute. The typical sample quantity is about 4 mg. As a typical distinguishing feature compared with the modifications B and C, the thermogram of the modification A has no further thermal signal.

Crystals of the modification A' have the same crystal structure as modification A. They differ from the modification A in the X-ray powder pattern in that they have slightly smaller line spacings between specific pairs of lines. These are the pairs of lines with the following interplanar spacings: 3.68 Å and 3.64 Å, 3.51 Å and 3.48 Å, 3.19 Å and 3.15 Å.

In the FT-IR spectrum (KBr pellet—transmission method), the novel modification B differs from the modification A or A' and C predominantly in the shape and in the relative intensity of many bands. Particularly characteristic is a band at 1678 cm$^{-1}$ [cf. FIG. 1], which is not to be observed in the corresponding spectra of the modifications A and C. In the range 4000-600 cm$^{-1}$, inter alia the following bands are obtained for the modification B: 3404, 3199, 3125, 1678, 1635, 1560, 1475, 1393, 1357, 1322, 1286, 1237, 1051, 1036, 1028, 889, 837, 800, 719, 667 and 645 cm$^{-1}$. For example, the apparatus IFS 85 (Bruker) can be used for recording of each of the FT-IR spectra.

In the FT Raman spectrum (powder—reflection method 180°), the novel modification B differs from the modifications A or A' and C predominantly in the shape and in the relative intensity of many bands. Particularly characteristic are the bands at 3166 cm$^{-1}$ and 1086 cm$^{-1}$ [cf. FIG. 2], which are not present in the Raman spectra of the modifications A and C. In the range 3400-300 cm$^{-1}$, inter alia the following bands are obtained for the modification B: 3166, 3089, 2970, 1678, 1628, 1614, 1559, 1464, 1441, 1391, 1275, 1244, 1147, 1086, 1062, 1036, 1014, 839, 773, 724, 690, 668, 595, 549, 500, 493, 430 and 365 cm$^{-1}$. For example, the apparatus RFS 100 (Bruker) can be used for recording of each of the FT Raman spectra.

The novel modification B has an X-ray powder pattern with characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å, 2.83 Å [cf. Table 1].

In the thermogram in differential scanning calorimetry, the novel modification B has, in addition to an endothermic signal in the range from 230° C. to 260° C. (peak temperature 239-245° C.), a weak thermal signal at 205° C. (180°-220° C.) as a typical distinguishing feature compared with the modifications A or A' and C.

In the FT-IR spectrum (KBr pellet—transmission method), the novel modification C differs from the modifications A or A' and B predominantly in the shape and in the relative intensity of many bands. Particularly characteristic is a band at 3137 cm$^{-1}$ [cf. FIG. 1], which is not to be observed in the corresponding spectra of the modifications A and B.

In the range 4000-600 cm$^{-1}$, inter alia the following bands are obtained for the novel modification C: 3396, 3287, 3137, 1657, 1631, 1602, 1559, 1475, 1392, 1323, 1287, 1237, 1122, 1104, 1047, 1035, 1012, 876, 839, 797, 773, 729 and 653 cm$^{-1}$. For example, the apparatus IFS 85 (Bruker) can be used for recording of each of the FT-IR spectra.

In the FT Raman spectrum (powder—reflection method 180°), the modification C differs from the modifications A or A' and B predominantly in the shape and in the relative intensity of many bands. Particularly characteristic are the bands at 3137 cm$^{-1}$ and 1602 cm$^{-1}$ [cf. FIG. 2], which are not present in the Raman spectra of the modifications A and B. In the range 3400-300 cm$^{-1}$, inter alia the following bands are obtained for the modification C: 3137, 3080, 3012, 2971, 1673, 1629, 1602, 1561, 1436, 1271, 1248, 1105, 1065, 1035, 1013, 839, 800, 767, 726, 690, 672, 593, 549, 500, 492, 435 and 370 cm$^{-1}$. For example, the apparatus RFS 100 (Bruker) can be used for recording of each of the FT Raman spectra.

The novel modification C has an X-ray powder pattern with characteristic lines with interplanar spacings (d values) of 9.0 Å, 4.73 Å, 4.65 Å, 3.75 Å, 3.54 Å, 3.42 Å, 3.25 Å [cf. Table 1]. In the thermogram in differential scanning calorimetry, the modification C has, in addition to an endothermic signal in the range of 230° C. to 260° C. (peak temperature 239-245° C.), a very broad, weak, exothermic signal in the region of 180° C. compared with the modifications A or A' and B.

TABLE 1

Characterization of the modifications A, B and C (X-ray powder patterns):

| Modification A: | | Modification B: | | Modification C: | |
| --- | --- | --- | --- | --- | --- |
| d [Å] | Intensity | d [Å] | Intensity | d [Å] | Intensity |
| 10.9 | weak | 11.0 | medium | 9.0 | medium |
| 10.5 | medium | 8.3 | medium | 7.0 | weak |
| 6.6 | weak | 8.1 | very weak | 5.49 | weak |
| 5.63 | weak | 5.68 | very weak | 5.11 | very weak |
| 5.25 | weak | 5.18 | very strong | 4.80 | weak |
| 5.14 | medium | 5.11 | weak | 4.73 | strong |
| 4.94 | weak | 4.88 | medium | 4.65 | very strong |
| 4.84 | very strong | 4.80 | strong | 4.47 | very weak |
| 4.55 | strong | 4.71 | very weak | 4.19 | very weak |
| 4.42 | very weak | 4.61 | weak | 4.11 | very weak |
| 4.34 | medium | 4.45 | weak | 3.98 | very weak |
| 4.23 | very weak | 4.42 | strong | 3.83 | very weak |
| 4.16 | weak | 4.33 | very strong | 3.75 | strong |
| 4.07 | medium | 4.19 | medium | 3.73 | weak |
| 4.01 | weak | 4.12 | strong | 3.54 | medium |
| 3.68 | very weak | 4.09 | weak | 3.50 | weak |
| 3.64 | very weak | 3.99 | very weak | 3.42 | strong |
| 3.60 | weak | 3.95 | very weak | 3.25 | medium |
| 3.56 | weak | 3.84 | weak | 2.88 | very weak |
| 3.51 | medium | 3.81 | medium | 2.80 | very weak |
| 3.48 | medium | 3.65 | weak | 2.74 | very weak |
| 3.38 | very weak | 3.61 | very weak | 2.67 | very weak |
| 3.25 | strong | 3.58 | very weak | 2.64 | weak |
| 3.19 | medium | 3.54 | weak | | |
| 3.15 | medium | 3.50 | medium | | |
| 3.11 | weak | 3.47 | very weak | | |
| 3.07 | medium | 3.41 | medium | | |
| 2.93 | very weak | 3.36 | very strong | | |
| 2.87 | very weak | 3.32 | strong | | |
| 2.81 | medium | 3.28 | medium | | |
| 2.76 | weak | 3.24 | medium | | |
| 2.73 | very weak | 3.10 | weak | | |
| 2.68 | weak | 3.07 | weak | | |
| 2.62 | very weak | 3.05 | medium | | |
| 2.53 | weak | 2.93 | weak | | |
| 2.43 | weak | 2.88 | weak | | |
| 2.40 | very weak | 2.87 | very weak | | |
| | | 2.83 | medium | | |
| | | 2.66 | weak | | |
| | | 2.63 | very weak | | |
| | | 2.55 | weak | | |
| | | 2.50 | weak | | |
| | | 2.46 | weak | | |
| | | 2.44 | weak | | |
| | | 2.37 | weak | | |
| | | 2.35 | weak | | |

Single Crystal X-ray Analysis:

Crystal quality and unit cell of modifications A, B, and C were verified by Weissenberg and precession photographs. The intensities were measured on a four-axis Nonius CAD-4 diffractometer. The structures were solved with the SHELXS-97 and refined with the SHELXL-97 software.

Modification A
  Space group: Pna2$_1$-orthorhombic
  Cell dimensions:

| a = 24.756 (5) Å | b = 23.069 (4) Å | c = 5.386 (1) Å |
| --- | --- | --- |
| v = 3075.9 Å$^3$ | Z = 12 | D$_x$ = 1.543 gcm$^{-3}$ |
| v per formula: | V$_z$ = 256.3 Å$^3$ | |

9011 unique reflections; 2479 thereof significant with I>2σ(I). 557 parameters refined.

Position of all H atoms found by difference Fourier maps and refined isotropically.

Reliability index $R_1$: 3.65% ($wR_2$ for all 9011 reflections: 11.34%).

Modification B
Space group: P⁻1-triclinic
Cell dimensions:

| | | |
|---|---|---|
| a = 5.326 (1) Å | b = 11.976 (2) Å | c = 17.355 (3) Å |
| α = 107.22 (3)° | β = 92.17 (3)° | γ = 102.11 (3)° |
| v = 1027.9 Å³ | Z = 4 | $D_x$ = 1.539 gcm⁻³ |
| v per formula | $V_z$ = 257.0 Å³ | |

4934 unique reflections; 834 thereof significant with I>2σ (I). 232 parameters refined.

Position of all H atoms found by difference Fourier maps and refined isotropically.

Reliability index $R_1$: 4.20% ($wR_2$ for all 4934 reflections: 7.93%).

Modification C
Space group: P2₁/C-monoclinic
Cell dimensions:

| | | |
|---|---|---|
| a = 10.982 (2) Å | b = 5.350 (1) Å | c = 17.945 (3) Å |
| v = 1053.9 Å³ | β = 91.59 (1)° | $D_x$ = 1.501 gcm⁻³ |
| v per formula: | Z = 4 | |
| | $V_z$ = 263.5 Å³ | |

3073 unique reflections; 1071 thereof significant with I>2σ (I). 187 parameters refined.

Position of all H atoms found by difference Fourier maps and refined isotropically.

Reliability index $R_1$: 5.02% ($wR_2$ for all 3073 reflections: 14.55%).

Modifications A, A', B and C have valuable pharmacological properties; in particular, they can be used for the treatment of epilepsy.

The modification A or A' has significant advantages compared with the modification B and compared with the modification C. Thus, for example, comprehensive thermodynamic investigations, such as thermomicroscopy, X-ray powder diffractometry, DSC, solubility tests and other experiments, have shown that the modification A or A' surprisingly has substantially better thermodynamic stability than the modifications B and C.

Modification C, which can be obtained only under specific conditions, is the least stable of the three modifications. The crystals of the modification C are converted into modification B at as low as room temperature within a few weeks. The modification C is converted either into the modification A or A' or into the modification B, depending on experimental conditions.

It is particularly important for a drug that its pharmaceutical formulation ensures high and reproducible stability over a long period. These preconditions are fulfilled by incorporation of the compound 1-(2,6-difluorobenzyl)-1H-1,2,3-triazole-4-carboxamide of the crystal modification A or A', owing to its high thermodynamic stability. In particular, this is displayed in a solid pharmaceutical dosage form.

A constant stability also permits reproducible bioavailability of an active ingredient. If an active ingredient is subjected to a conversion process, this may readily also cause the bioavailability to fluctuate, which is undesirable. Accordingly, pharmaceutical active ingredients or polymorphic forms thereof which are of primary interest for pharmaceutical developments are those which exhibit high stability and do not have the above-mentioned disadvantages. The crystal modification A or A' fulfills these preconditions.

Furthermore, the modification A or A' has, for example, a slower dissolution rate in water or in gastric fluid (so-called "slow-release effect"). This effect can be utilized primarily for long-term therapy where a slow or delayed release is desired.

The invention relates to the modification A of 1-(2,6-difluorobenzyl)-1H- 1,2,3-triazole-4-carboxamide, characterized by the following absorptions in the infrared spectrum (KBr pellet—transmission method): bands at 3092 cm⁻¹ and 3412 cm⁻¹.

The invention relates to the modification A of 1-(2,6-difluorobenzyl)-1H-1,2,3-triazole-4-carboxamide, characterized by characteristic lines with interplanar spacings (d values) of 10.5 Å, 5.14 Å, 4.84 Å, 4.55 Å, 4.34 Å, 4.07 Å, 3.51 Å, 3.48 Å; 3.25 Å, 3.19 Å, 3.15 Å, 3.07 Å and 2.81 Å, determined by means of an X-ray powder pattern.

The invention relates to the modification A of 1-(2,6-difluorobenzyl)-1H-1,2,3-triazole-4-carboxamide, characterized by the characteristic lines with interplanar spacings (d values) as shown in Table 1.

The invention relates to the modification A of 1-(2,6-difluorobenzyl)-1H-1,2,3-triazole-4-carboxamide, characterized by an endothermic peak in the range from 230°C. to 260 °C., the peak temperature being 239-245 °C. and the endothermic signal being 209 J/g +/−10 J/g.

Furthermore, the invention relates to the crystal modification A' which, compared with modification A, has defects in the crystal lattice.

The invention relates to the modification A' which, compared with modification A, has smaller line spacings between the pairs of lines with interplanar spacings 3.68 Å and 3.64 Å, 3.51 Å and 3.48 Å, and 3.19 Å and 3.15 Å.

The invention relates to the essentially pure form of the modification A or A' of 1-(2,6-difluorobenzyl)-1H-1,2,3-triazole-4-carboxamide. The term "essentially pure form" means purity of >95%, in particular >98%, primarily >99%, based on the modification A or A'.

The invention relates to pharmaceutical preparations comprising the modification A or A' of 1-(2,6-difluorobenzyl)-1H-1,2,3-triazole-4-carboxamide. The invention relates in particular to corresponding pharmaceutical preparations for the treatment of epilepsy and subindications thereof. The invention relates to the use of the modification A or A' of 1-(2,6-difluorobenzyl )-1H-1,2,3-triazole-4-carboxamide for the preparation of pharmaceutical preparations, in particular for the treatment of epilepsy and subindications thereof.

The novel modification A or A' of 1-(2,6-difluorobenzyl)-1H-1,2,3-triazole-4-carboxamide can be used, for example, in the form of pharmaceutical preparations which comprise a therapeutically effective amount of the active ingredient, if desired together with inorganic or organic, solid or liquid, pharmaceutically usable carriers, which are suitable for enteral, for example oral, or parenteral administration.

Furthermore, the novel modification A or A' of 1-(2,6-difluorobenzyl)-1H-1,2,3-triazole-4-carboxamide can be used in the form of preparations which can be administered parenterally or of infusion solutions. The pharmaceutical preparations may be sterilized and/or may comprise excipients, for example preservatives, stabilizers, wetting agents and/or emulsifiers, solubilizers, salts for regulating the osmotic pressure and/or buffers. The present pharmaceutical preparations comprise from about 0.1% to 100%, in particular from about 1% to about 50%, of lyophilisates to about 100% of the active ingredient.

The invention also relates to the use of modification A or A' of 1-(2,6-difluorobenzyl)-1H-1,2,3-triazole-4-carboxamide as a drug, preferably in the form of pharmaceutical preparations. The dosage may depend on various factors, such as method of administration, species, age and/or individual condition. The doses to be administered daily are between about 0.25 and about 10 mg/kg in the case of oral administration, and preferably between about 20 mg and about 500 mg for warm-blooded species having a body weight of about 70 kg.

The preparation of modification A or A' is carried out, for example, as described in the embodiments below.

EXAMPLE 1

Modification A

A suspension of methyl 1-(2,6-difluorobenzyl)-1H-1,2,3-triazole-4-carboxylate (about 62 parts by weight), methanol (475.2 parts by weight) and anhydrous ammonia (29.4 parts by weight) is stirred for about 24 hours at 50-55°C. in a closed vessel. The suspension is cooled to about 20°C. and stirred for about a further 2 hours. The product is isolated by filtration, washed with methanol (240 parts by weight) and dried at 40-60°C. in vacuo. Yield: 57.2 parts by weight =98% modification A.

The starting compounds can be prepared, for example, as follows:

A mixture of 1-(2,6-difluorobenzyl)-1H-1,2,3-triazole-4-carboxylic acid (167.1 parts by weight), methanol (552 parts by weight) and 96% sulfuric acid (35.7 parts by weight) is stirred for about 5 hours at 60-66°C. The suspension is cooled to about 20°C. and stirred for about a further 2 hours. The product is isolated by filtration and washed with methanol (198 parts by weight). A yield of about 160 parts by weight is obtained by drying at 40-60°C. in vacuo.

EXAMPLE 2

Modification A

1 N sodium hydroxide solution (0.11 ml) is added to a mixture of 4-cyano-1-(2,6-difluorobenzyl)-1H-1,2,3-triazole (2.20 g) and water (44 ml) at an external temperature of 95-100°C. while stirring. After 90 minutes, the suspension is cooled to 10°C. and the product is isolated by filtration, washed with water and dried at about 60°C. in vacuo. 1-(2,6-Difluorobenzyl)-1H-1,2,3-triazole-4-carboxamide is obtained in this manner; yield: 99.2% by weight modification A.

The starting material can be prepared, for example, as follows:

4-Cyano-1-(2,6-difluorobenzyl)-1H-1,2,3-triazole: A mixture of 2,6-difluorobenzyl azide (34.2 g), 2-chloroacrylonitrile (17.73 g) and water (125 ml) is stirred for 24 hours at about 80°C. By increasing the external temperature to about 130°C., excess 2-chloroacrylonitrile is distilled off. The semisolid mixture is cooled to about 40°C., cyclohexane (50 ml) is added to the suspension and the mixture is brought to about 20°C. and stirred for about 2 hours. The product is isolated by filtration and washed with cyclohexane (75 ml) and then with water (50 ml). The moist product is mixed with water (100 ml), the suspension is filtered and the product is washed with water (50 ml) and dried at about 60°C. in vacuo. Yield: 38.04 g =86%.

EXAMPLE 3

Re-crystallization of 1-(2.6-difluorobenzyl-1H-1,2,3-triazole-4-carboxamide 1-(2,6-Difluorobenzyl)-1H-1,2,3-triazole-4-carboxamide (75.0 g) is dissolved in formic acid (360 ml) at 50-55°C. by stirring. The solution is discharged in the course of 1 hour onto stirred methanol (375 ml) at about 20°C., a suspension forming. After stirring has been continued for 2 hours at about 20°C., the product is isolated by filtration, washed with methanol (750 ml) and dried at about 60°C. in vacuo. Yield: 69.6 g =92.8% modification A.

EXAMPLE 4

Re-crystallization of 1-(2.6-difluorobenzyl-1H-1,2,3-triazole-4-carboxamide 1-(2,6-Difluorobenzyl)- 1H-1,2,3-triazole-4-carboxamide (22.86 kg) is dissolved in formic acid (111.6 kg) at 58-63°C. while stirring. The solution is discharged in the course of about 2 hours onto stirred methanol (131.9 l) at 20-25°C., after which washing with formic acid (7.6 kg) is carried out. A suspension forms. After stirring has been continued for at least 3 hours at about 20°C. the product is isolated by filtration and washed with methanol (187.5 l). By drying in vacuo at about 60°C., the product is obtained as modification A in a yield of 93-94%.

EXAMPLE 5

Modification A'

1-(2,6-difluorobenzyl)-1H-1,2,3-triazole-4-carboxamide (pure active ingredient; 4.0 g) is dissolved in 96% ethanol (500 ml, without denaturing agent) at about 80°C. while stirring. The solution is filtered into a suction bottle (1 liter) at about 20°C. (glass suction filter, pore size 10-20 μm), a suspension forming. After stirring has been continued for 5 minutes at about 20°C. and for 15 minutes at about 0°C.,the product is isolated by filtration (about 0° to about 20°C.). The solvent-moist product (9.6 g) is investigated without subsequent drying.

EXAMPLE 6

Modification Form A or A' Formulation Example

Film-coated tablets each containing, for example, 100, 200 or 400 mg of modification A or A' of 1-(2,6-difluorobenzyl)-1H-1,2,3-triazole-4-carboxamide with the following composition per dosage unit:

|  | mg | mg | mg |
|---|---|---|---|
| Core material |  |  |  |
| Active ingredient | 100.00 | 200.00 | 400.00 |
| Anhydrous, colloidal silica | 0.88 | 1.75 | 3.5 |
| Microcrystalline cellulose | 36.62 | 73.25 | 146.50 |
| Hydroxypropylmethyl-cellulose | 5.00 | 10.00 | 20.00 |

-continued

|  | mg | mg | mg |
|---|---|---|---|
| Lactose | 20.00 | 40.00 | 80.00 |
| Magnesium stearate | 2.00 | 4.00 | 8.00 |
| Maize starch | 10.00 | 20.00 | 40.00 |
| Sodium carboxymethyl-cellulose | 5.00 | 10.00 | 20.00 |
| Sodium laurylsulfate | 0.50 | 1.00 | 2.00 |
| Film coat |  |  |  |
| Hydroxypropylmethyl-cellulose | 3.22 | 6.43 | 12.87 |
| Red iron oxide | 0.04 | 0.09 | 0.18 |
| Polyethylene glycol 8000, flakes | 0.58 | 1.16 | 2.32 |
| Talc | 2.33 | 4.66 | 9.31 |
| Titanium dioxide | 0.83 | 1.66 | 3.32 |

The active ingredient is granulated with demineralized water. Milled lactose, maize starch, Avicel PH 102, cellulose-HP-M-603 and sodium laurylsulfate are added to the above mixture and granulated with demineralized water.

The moist material is dried and milled. After the addition of the remaining ingredients, the homogeneous mixture is compressed to give tablet cores having the stated active ingredient content.

The tablet cores are coated with the film coat which is formed from the appropriate ingredients, the latter being dissolved or being suspended in water or in small amounts of ethanol with 5% of isopropanol.

The modifications B and C have significant advantages compared with the modification A or A'.

Thus, it was found, for example, that modification B has a substantially faster dissolution rate in water and gastric fluid than modification A or A'. Consequently, when modification B is used therapeutically, a rapid onset of action is achieved, which is particularly advantageous, for example in an acute epilepsy attack.

The invention relates to the modification B of 1-(2,6-difluorobenzyl)-1H-1,2,3-triazole-4-carboxamide, having the following absorption in the infrared spectrum (KBr pellet—transmission method): band at 1678 $cm^{-1}$.

The invention relates to the modification B of 1-(2,6-difluorobenzyl)-1H-1,2,3-triazole-4-carboxamide, having characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å and 2.83 Å, determined by means of an X-ray powder pattern.

The invention relates to the modification B of 1-(2,6-difluorobenzyl)-1H-1,2,3-triazole-4-carboxamide, having the characteristic lines with interplanar spacings (d values) as shown in Table 1.

The invention relates to the modification B of 1-(2,6-difluorobenzyl)-1H-1,2,3-triazole-4-carboxamide, having in the thermogram in differential scanning calorimetry a weak thermal signal at 205° C. (180-220° C.) in addition to an endothermic signal in the range from 230° C. to 260° C. (peak temperature 239-245° C.).

The invention furthermore relates to the crystal modification C of 1-(2,6-difluorobenzyl)-1H-1,2,3-triazole-4-carboxamide, having the following absorption in the infrared spectrum (KBr pellet—transmission method): band at 3137 $cm^{-1}$.

The invention relates to the modification C of 1-(2,6-difluorobenzyl)-1H-1,2,3-triazole-4-carboxamide, having characteristic lines with interplanar spacings (d values) of 9.0 Å, 4.73 Å, 4.65 Å, 3.75 Å, 3.54 Å, 3.42 Å, 3.25 Å, determined by means of an X-ray powder pattern.

The invention relates to modification C of 1-(2,6-difluorobenzyl)-1H-1,2,3-triazole-4-carboxamide, having the characteristic lines with interplanar spacings (d values) as shown in Table 1.

The invention relates to the modification C of 1-(2,6-difluorobenzyl)-1H-1,2,3-triazole-4-carboxamide, having in the thermogram in differential scanning calorimetry a very broad weak exothermic signal in the region of 180° C., in addition to an endothermic signal in the range from 230° C.-260° C. (peak temperature 239-245° C.).

The invention relates to the essentially pure forms of the modifications B and C of 1-(2,6-difluorobenzyl)-1H-1,2,3-triazole-4-carboxamide. The term "essentially pure form" means purity of >95%, in particular >98%, primarily >99%, based on the modifications B and C.

The invention relates to pharmaceutical preparations comprising the modifications B and C of 1-(2,6-difluorobenzyl)-1H-1,2,3-triazole-4-carboxamide. The invention relates in particular to corresponding pharmaceutical preparations for the treatment of epilepsy and subindications thereof. The invention relates to the use of the modifications B and C of 1(2,6-difluorobenzyl)-1H-1,2,3-triazole-4-carboxamide for the preparation of pharmaceutical preparations, in particular for the treatment of epilepsy and subindications thereof.

The novel modifications B and C of 1-(2,6-difluorobenzyl)-1H-1,2,3-triazole-4-carboxamide can be used, for example, in the form of pharmaceutical preparations which comprise a therapeutically effective amount of the active ingredient, if desired together with inorganic or organic, solid or liquid, pharmaceutically usable carriers, which are suitable for enteral, for example oral, or parenteral administration. Furthermore, the novel modifications B and C of 1-(2,6-difluorobenzyl)-1H-1,2,3-triazole-4-carboxamide can be used in the form of preparations which can be administered parenterally or of infusion solutions. The pharmaceutical preparations may be sterilized and/or may comprise excipients, for example preservatives, stabilizers, wetting agents and/or emulsifiers, solubilizers, salts for regulating the osmotic pressure and/or buffers. The present pharmaceutical preparations comprise from about 0.1% to 100%, inparticular from about 1% to about 50%, of lyophilisates to about 100% of the active ingredient.

The invention also relates to the use of the rhodifications B and C of 1-(2,6-difluorobenzyl)-1H-1,2,3-triazole-4-carboxamide as a drug, preferably in the form of pharmaceutical preparations. The dosage may depend on various factors, such as method of administration, species, age and/or individual condition. The doses to be administered daily are between about 0.25 and about 10 mg/kg in the case of oral administration, and preferably between about 20 mg and about 500 mg for warm-blooded species having a body weight of about 70 kg.

The preparation of the modifications B and C is carried out, for example, as described in the embodiments below.

EXAMPLE 7

Modification B 1-(2,6-Difluorobenzyl)-1H-1,2,3-triazole4-carboxamide (18.29 kg) is dissolved in formic acid (89.3 kg) at 58-63° C. while stirring. The solution is discharged in the course of about 30 minutes onto stirred methanol (105.5l) at 20° C. to 0° C., after which washing with formic acid (6.1 kg) is carried out. A suspension forms. The product is isolated immediately by filtration and washed with cold methanol (150 l, about 4°

C.). By drying in vacuo at about 60° C., the product is obtained as modification B in a yield of about 94%.

EXAMPLE 8

Modification C 1-(2,6-Difluorobenzyl)-1H-1,2,3-triazole-4-carboxamide (15.0 g) is dissolved in acetic acid (120 ml) at about 90° C. while stirring. The solution is cooled to 20° C. in the course of about 8 minutes, a suspension forming. The product is immediately isolated by filtration, washed with toluene (120 ml) and dried in vacuo at about 60° C.10.1 g of the product are obtained as modification C. Yield 67.3%.

EXAMPLE 9

Modification Form B or C Formulation Example

Film-coated tablets each containing, for example, 100, 200 or 400 mg of the modification B or C of 1-(2,6-difluorobenzyl)-1H-1,2,3-triazole-4-carboxamide with the following composition per dosage unit:

| Core material | mg | mg | mg |
|---|---|---|---|
| Active ingredient | 100.00 | 200.00 | 400.00 |
| Anhydrous, colloidal silica | 0.88 | 1.75 | 3.5 |
| Microcrystalline cellulose | 36.62 | 73.25 | 146.50 |
| Hydroxypropylmethyl-cellulose | 5.00 | 10.00 | 20.00 |
| Lactose | 20.00 | 40.00 | 80.00 |
| Magnesium stearate | 2.00 | 4.00 | 8.00 |
| Maize starch | 10.00 | 20.00 | 40.00 |
| Sodium carboxymethyl-cellulose | 5.00 | 10.00 | 20.00 |
| Sodium laurylsulfate | 0.50 | 1.00 | 2.00 |

| Film coat | mg | mg | mg |
|---|---|---|---|
| Hydroxypropylmethyl-cellulose | 3.22 | 6.43 | 12.87 |
| Red iron oxide | 0.04 | 0.09 | 0.18 |
| Polyethylene glycol 8000, flakes | 0.58 | 1.16 | 2.32 |
| Talc | 2.33 | 4.66 | 9.31 |
| Titanium dioxide | 0.83 | 1.66 | 3.32 |

The active ingredient is granulated with demineralized water. Milled lactose, maize starch, Avicel PH 102, cellulose-HP-M-603 and sodium laurylsulfate are added to the above mixture and granulated with demineralized water.

The moist material is dried and milled. After the addition of the remaining ingredients, the homogeneous mixture is compressed to give tablet cores having the stated active ingredient content.

The tablet cores are coated with the film coat which is formed from the appropriate ingredients, the latter being dissolved or being suspended in water or in small amounts of ethanol with 5% of isopropanol.

Figure 1:
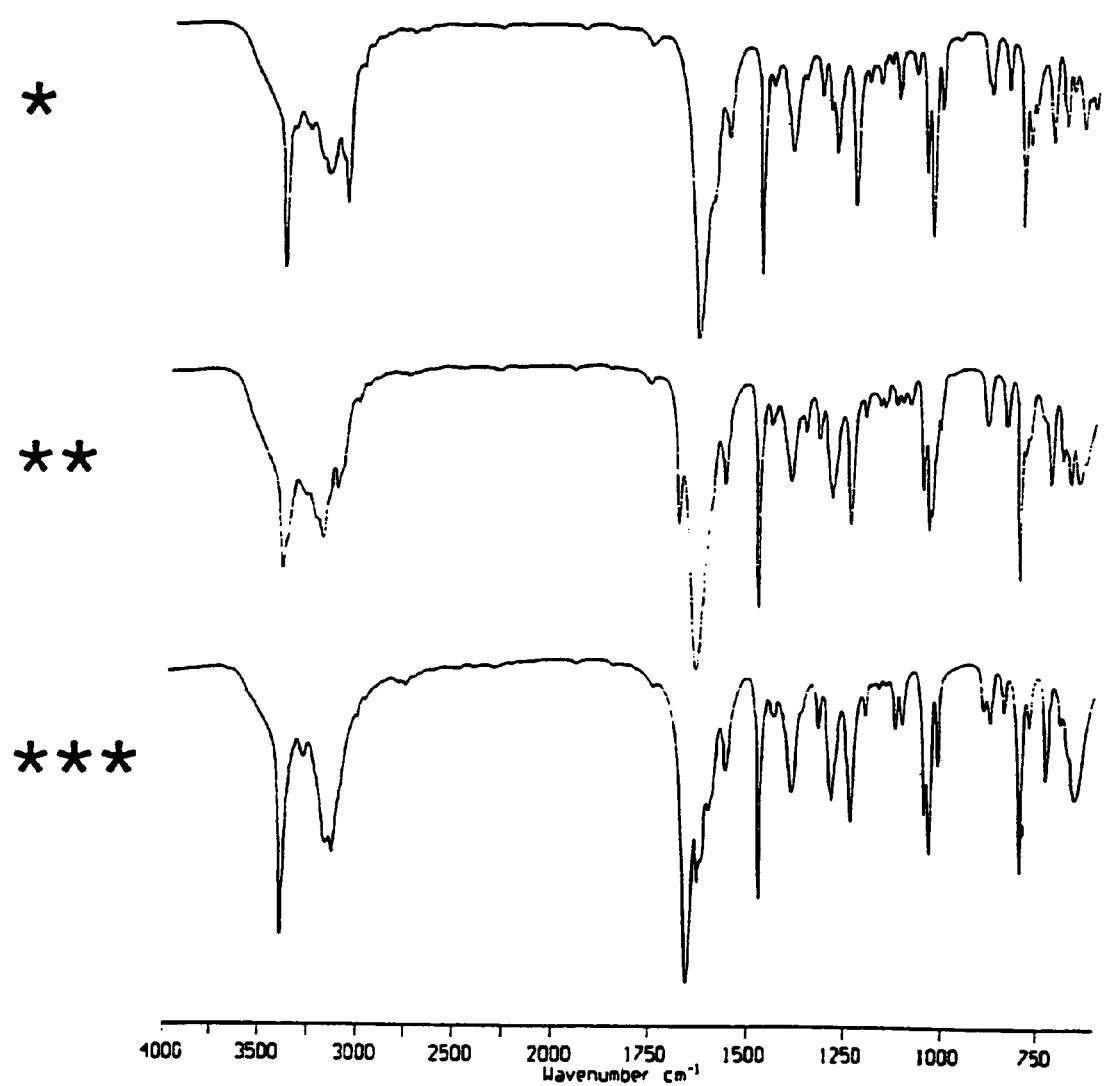
FIG. 1 shows the FT-IR spectra of the KBr pellets of crystal modifications A, B and C.
Figure 2:
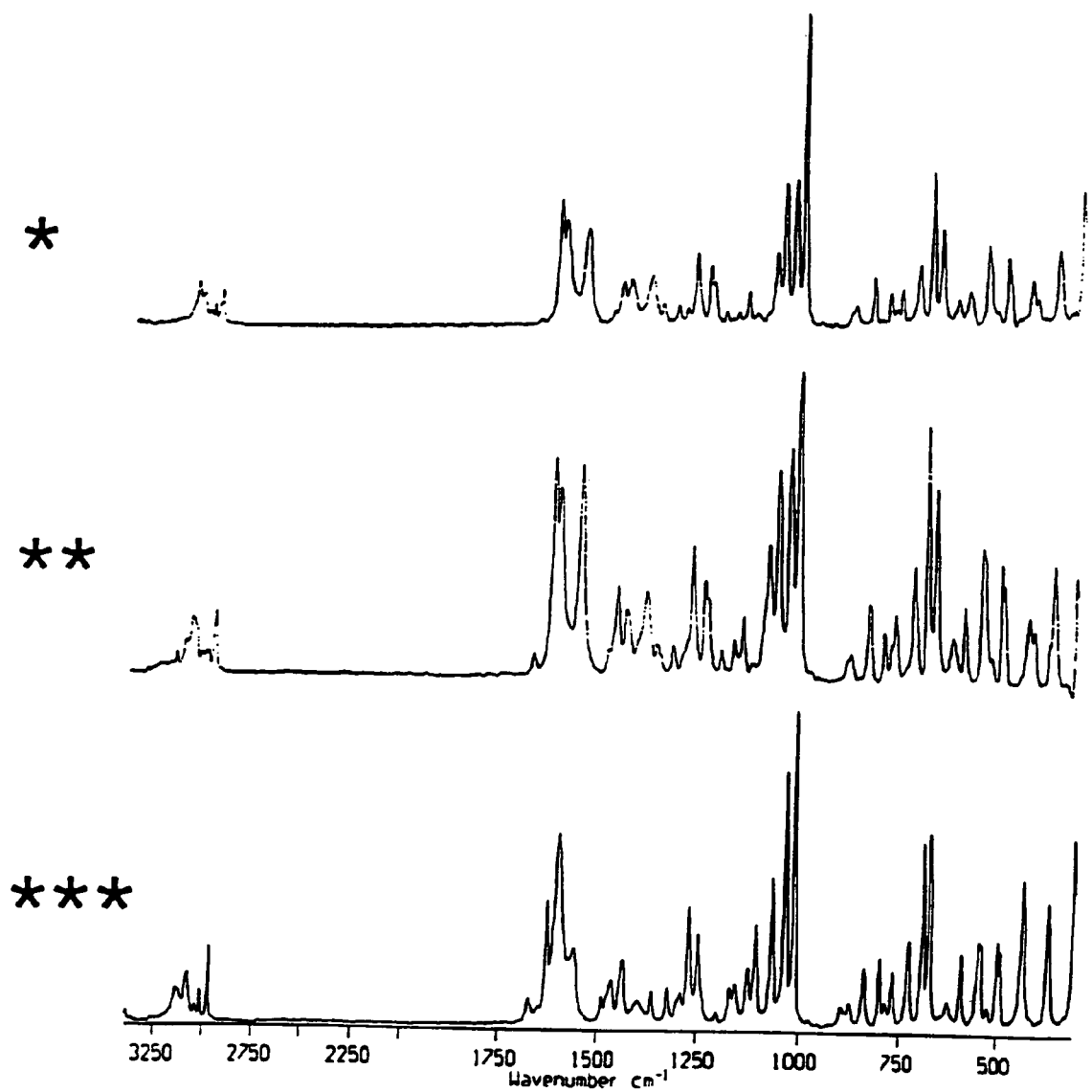
FIG. 2 shows the FT-Raman spectra of the powder of modifications A, B and C.

In both Figures, the modification A is denoted by the symbol *, the modification B by the symbol  and the modification C by the symbol *.

What is claimed is:

1. A method of treating epilepsy comprising administering to a subject in need of such treatment a pharmaceutical composition, comprising a pharmaceutically acceptable carrier or diluent and a therapeutically effective amount of crystal modification A of the compound 1-(2,6-difluorobenzyl)-1 H-1,2,3-triazole-4-carboxamide of the formula

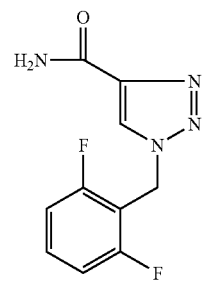

characterized by characteristic lines at interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å and 2.81 Å, as determined by means of an X-ray powder pattern.

2. A method according to claim 1 comprising administering a pharmaceutical composition, comprising a pharmaceutically acceptable carrier or diluent and a therapeutically effective amount of crystal modification A of the compound 1 -(2,6-difluorobenzyl )-1H-1,2,3-triazole-4-carboxamide characterized by an X-ray powder pattern having the following characteristic lines at interplanar spacings (d values) of 10.9 Å (weak), 10.5 Å (medium), 6.6 Å (weak), 5.63 Å (weak), 5.25 Å (weak), 5.14 Å (medium). 4.94 Å (weak), 4.84 Å (very strong), 4.55 Å (strong), 4.42 Å (very weak), 4.34 Å (medium), 4.23 Å (very weak), 4.16 Å (weak), 4.07 Å (medium), 4.01 Å (weak), 3.68 Å (very weak), 3.64 Å (very weak), 3.60 Å (weak), 3.56 Å (weak), 3-51 Å (medium), 3.48 Å (medium), 3.38 Å (very weak), 3.25 Å (strong), 3.19 Å (medium), 3.15 Å (medium), 3.11 Å (weak), 3.07 Å (medium), 2.93 Å (very weak), 2.87 Å (very weak), 2.81 Å (medium), 2.76 Å (weak), 2.73 Å (very weak), 2.68 Å (weak), 2.62 Å (very weak), 2.53 Å (weak), 2,43 Å (weak) and 2.40 Å (very weak).

3. A method according to claim 1 comprising administering a pharmaceutical composition, comprising a pharmaceutically acceptable carrier or diluent and a therapeutically effective amount of crystal modification A of the compound 1 -(2,6-difluorobenzyl)-1 H-1,2,3-triazole-4-carboxamide characterized by absorption bands at 3412 cm$^{-1}$ and 3092 cm$^{-1}$ in the FT-IR spectrum (KBr pellet-transmission method).

4. A method according to claim 3 comprising administering a pharmaceutical composition, comprising a pharmaceutically acceptable carrier or diluent and a therapeutically effective amount of crystal modification A of the compound 1-(2,6-difluorobenzyl)-IH-1,2,3-triazole-4-carboxamide characterized by the following absorption bands in the FT-IR spectrum (KBr pellet-transmission method): 3412, 3189, 3092, 1634, 1560, 1473, 1397, 1325, 1300, 1284, 1235, 1125, 1053, 1036, 1014, 885, 840, 799, 781, 723, 688 and 640 cm$^{-1}$.

5. A method according to claim 1 comprising administering a pharmaceutical composition, comprising a pharmaceutically acceptable carrier or diluent and a therapeutically effective amount of crystal modification A of the compound 1-(2.6-difluorobenzyl)-1 H-1,2,3-triazole-4-carboxamide characterized by an endothermic peak in the range from 230° C. to 260° C., the peak temperature being 239-245° C. and the endothermic signal being 209 J/g ±10 J/g.

6. A method according to claim 1 comprising administering a pharmaceutical composition, comprising a pharmaceutically acceptable carrier or diluent and a therapeutically effective amount of crystal modification A of the compound 1-(2,6-difluorobenzyl)-1H-1,2,3-triazole-4-carboxamide characterized by an absorption band at 1080 cm$^{-1}$ in the FT-Raman spectrum.

7. A method according to claim 6 comprising administering a pharmaceutical composition, comprising a pharmaceutically acceptable carrier or diluent and a therapeutically effective amount of crystal modification A of the compound 1-(2,6-difluorobenzyl)-1 H-1,2,3-triazole-4-carboxamide characterized by the following absorption bands in the FT-Raman spectrum (powder-reflection method 180°): 3093, 2972, 1628, 1614, 1558, 1466, 1446, 1393, 1279, 1245, 1147, 1080, 1061, 1036, 1014, 840, 724, 691, 667, 550, 499, 437 and 368 cm$^{-1}$.

8. A method according to claim 1 comprising administering a pharmaceutical composition, comprising a pharmaceutically acceptable carrier or diluent and a therapeutically effective amount of crystal modification A of the compound 1-(2.8-difluorobenzyl)-1 H-1,2,3-triazole-4-carboxamide in essentially pure form.

* * * * *

UNITED STATES PATENT AND TRADEMARK OFFICE
CERTIFICATE OF CORRECTION

| | | |
|---|---|---|
| PATENT NO. | : 7,750,028 B2 | Page 1 of 1 |
| APPLICATION NO. | : 11/329945 | |
| DATED | : July 6, 2010 | |
| INVENTOR(S) | : Robert Portmann et al. | |

It is certified that error appears in the above-identified patent and that said Letters Patent is hereby corrected as shown below:

In the Claims

Column 14, line 13 (claim 8) change: "compound 1-(2.8-difluorobenzyl)-1 H-1,2,3-triazole-4-carboxamide in essentially pure form."

to

-- compound 1-(2,6-difluorobenzyl)-1 H-1,2,3-triazole-4-carboxamide in essentially pure form. --

Signed and Sealed this
Seventh Day of October, 2014

Michelle K. Lee
*Deputy Director of the United States Patent and Trademark Office*